United States Patent
Awaad et al.

(10) Patent No.: US 10,098,924 B1
(45) Date of Patent: Oct. 16, 2018

(54) **ANTICANCER EXTRACTS OF *ALPINIA OFFICINARUM* HANCE**

(71) Applicant: KING SAUD UNIVERSITY, Riyadh (SA)

(72) Inventors: Amani Shafeek Awaad, Riyadh (SA); Menatallah Mohamed Allah, Riyadh (SA); Lara Ayman El-Sawaf, Riyadh (SA); Reham Mostafa El-Meligy, Riyadh (SA); Fatmah Ali Al-Asamary, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/878,367

(22) Filed: Jan. 23, 2018

(51) Int. Cl.
*A61K 36/00* (2006.01)
*A61K 36/9062* (2006.01)
*A61P 35/00* (2006.01)

(52) U.S. Cl.
CPC ........ *A61K 36/9062* (2013.01); *A61P 35/00* (2018.01); *A61K 2236/13* (2013.01); *A61K 2236/15* (2013.01); *A61K 2236/17* (2013.01); *A61K 2236/33* (2013.01); *A61K 2236/39* (2013.01); *A61K 2236/51* (2013.01)

(58) Field of Classification Search
CPC .................................................. A61K 36/00
See application file for complete search history.

(56) References Cited

FOREIGN PATENT DOCUMENTS

| CN | 1799616 A | * | 7/2006 |
| CN | 101804175 A | | 8/2010 |
| CN | 105214067 A | | 1/2016 |
| CN | 106937931 A | * | 7/2017 |
| KR | 2007079683 A | * | 8/2007 |

OTHER PUBLICATIONS

Basri, A.M., et al., "A Review on the Phamacological Activities and Phytochemicals of *Alpinia officinarum* (Galangal) Extracts Derived From Bioassay-Guided Fractionation and Isolation," Pharmacogn Rev. 11(21): pp. 43-56 (2017).

Tiwari, P., et al., "Phtochemical Screening and Extraction: A Review," Internationale Pharmaceutica Sciencia 1(1) pp. 98-106 (2011).

Ye, Y., et al., "1' S-1'-Acetoxychavicol Acetate Isolated From *Alpinia* Galanga Inhibits Human Immunodeficiency Virus Type 1 Replication by Blocking Rev Transport," Journal of general Virology (87) pp. 2047-2053 (2006).

* cited by examiner

*Primary Examiner* — Qiuwen Mi
(74) *Attorney, Agent, or Firm* — Richard C. Litman

(57) ABSTRACT

The anticancer extracts of *Alpinia officinarum* Hance are produced by percolation extraction of dried *Alpinia officinarum* Hance rhizomes in 95% ethanol. The extracts may then be concentrated, suspended in water, filtered, and lyophilized. The resulting anticancer extracts may be used to kill a variety of cancer cells, including lung cancer, colorectal cancer, colon cancer, cervical cancer, and prostate cancer.

4 Claims, 5 Drawing Sheets

ANTICANCER EXTRACTS OF *ALPINIA OFFICINARUM* HANCE

BACKGROUND

1. Field

The disclosure of the present patent application relates to plant extracts, and particularly to anticancer extracts of *Alpinia officinarum* Hance.

2. Description of the Related Art

Cancers are often fatal and have a demonstrated ability to either evade or develop resistance to traditional therapies. Common therapies include surgery, chemotherapy, and immunotherapy. Depending upon the type and location of the cancer, surgery is frequently either impossible or insufficient. Chemotherapy, radiation therapy, and immunotherapy have demonstrated significant potential for certain patients with certain cancers, but rarely offer a cure. Further, these treatments often produce harmful side effects, and may even prove fatal for some patients.

Plants are a common source of new medicines, including many pharmaceutical drugs currently used to treat cancer. Compounds isolated from plants include Irinotecan, Vincristine, and Paclitxel, amongst others.

Plants of the Zingiberaceae family are found in many Asian countries. Some members of this family have been used in traditional or herbal medicine, including as antiseptics, anti-allergic agents, and anti-itching agents. Plants of the genus *Alpina* are thought to be a potential source of many bioactive molecules, including alkaloids, steroids, sterols, glycosides, flavonoids, tannins, and triterpenoids. *Alpinia officinarum* Hance is a species of the Zingiberaceae family, which is widely used as a spice. The rhizomes of *Alpinia officinarum* Hance have been used in traditional medicine as a digestive aid and are prized for their aromatic flavors and scents.

Although chemotherapy, radiation, and surgery are effective in treating some forms of cancer, there is still a great need for other forms of therapy that have less risk and fewer side effects. Thus, anticancer extracts of *Alpinia officinarum* Hance solving the aforementioned problems is desired.

SUMMARY

The anticancer extracts of *Alpinia officinarum* Hance are ethanol extracts of dried *Alpinia officinarum* Hance rhizomes. The rhizomes may be washed, dried, and ground into a powder. The powder may be extracted by percolation in ethanol for two days. The mare is extracted four times by the same procedure, and the combined extracts are concentrated at low temperature and reduced pressure. The total alcohol may be concentrated into a gummy residue. The residue may then be suspended in water and filtered to produce an aqueous filtrate. The aqueous filtrate may be lyophilized to produce a dry sterile extract. This dry sterile extract may then be rehydrated in an appropriate volume of a liquid, such as water, to obtain a desired extract dose.

These extracts may be administered to a patient in need thereof to treat cancer by killing cancer cells or reducing growth of the cancer. The cancer cells may be human cancer cells. The cancer being targeted may be lung cancer, colon cancer, cervical cancer, or prostate cancer.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
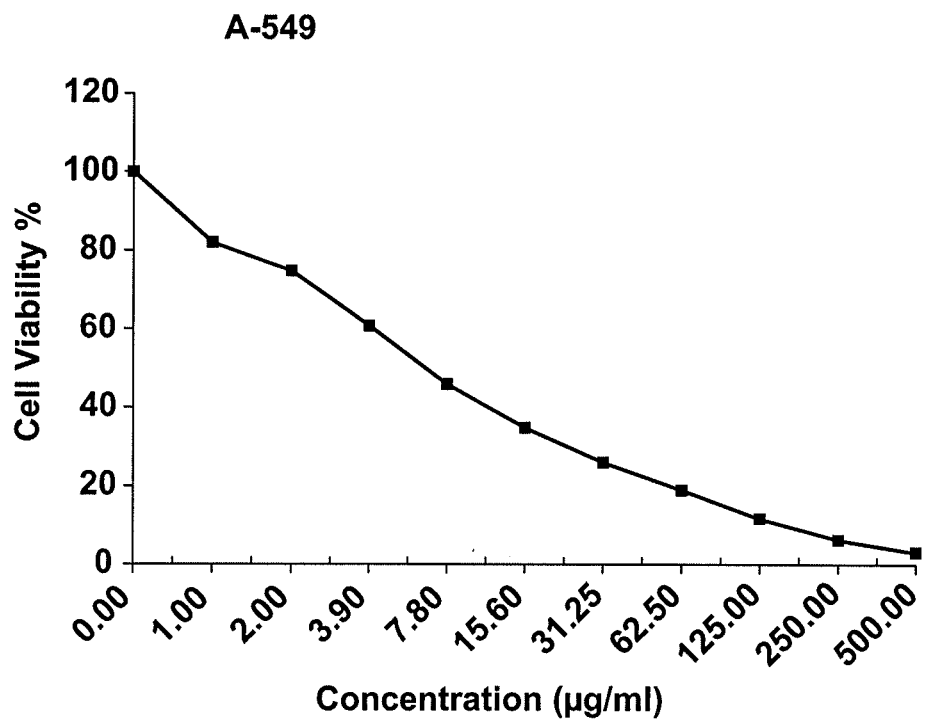
FIG. 1A is a graph of cell viability of A-549 (Lung carcinoma) cells exposed to different concentrations of anticancer extracts of *Alpinia officinarum* Hance.
Figure 1B:
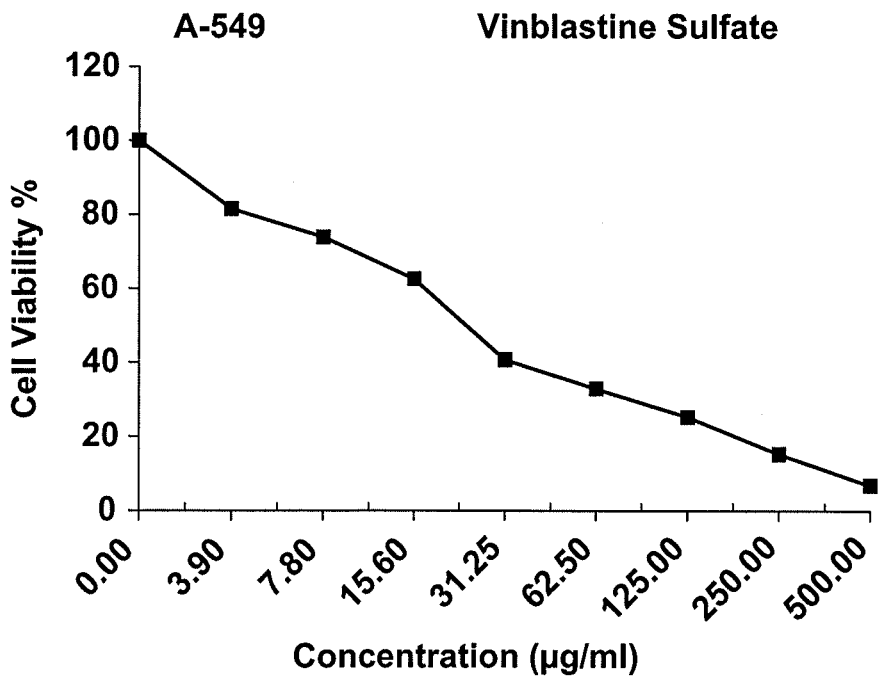
FIG. 1B is a graph of cell viability of A-549 cells exposed to different concentrations of the drug Vinblastine Sulfate.
Figure 2A:
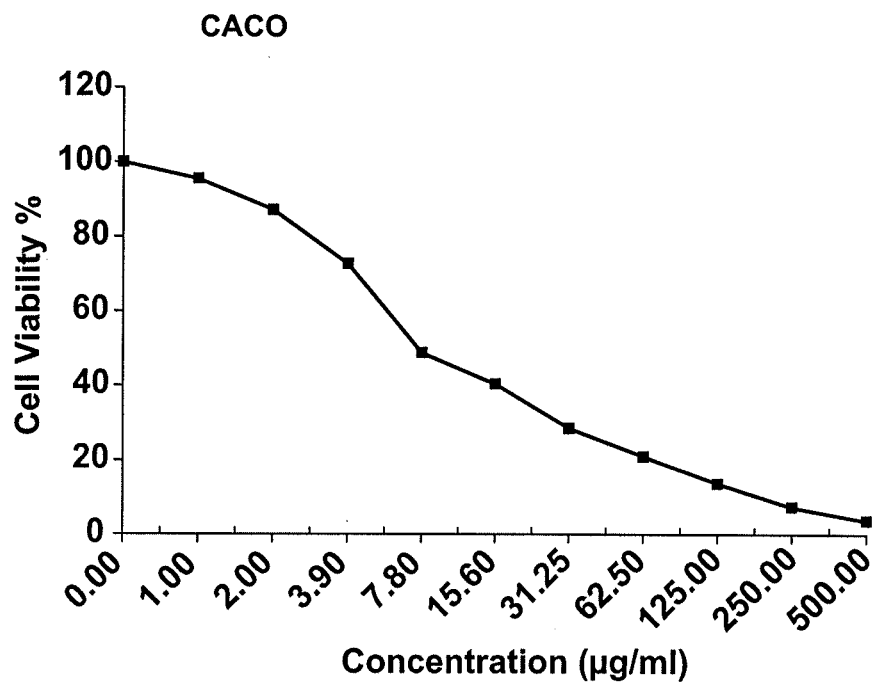
FIG. 2A is a graph of cell viability of CACO (colorectal carcinoma) cells exposed to different concentrations of anticancer extracts of *Alpinia officinarum* Hance.
Figure 2B:
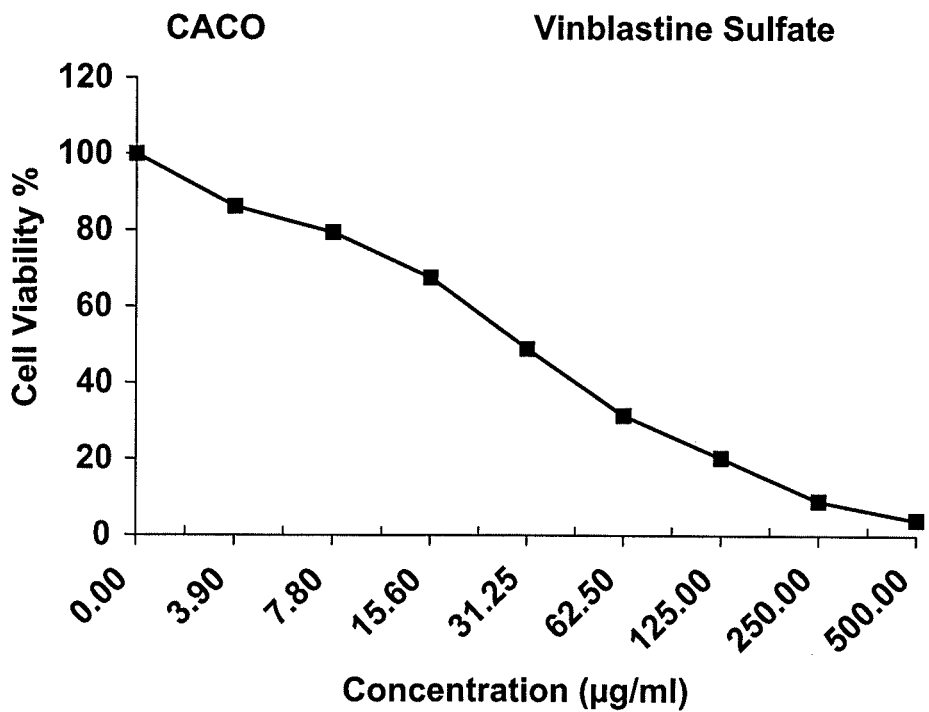
FIG. 2B is a graph of cell viability of CACO cells exposed to different concentrations of the drug Vinblastine Sulfate.
Figure 3A:
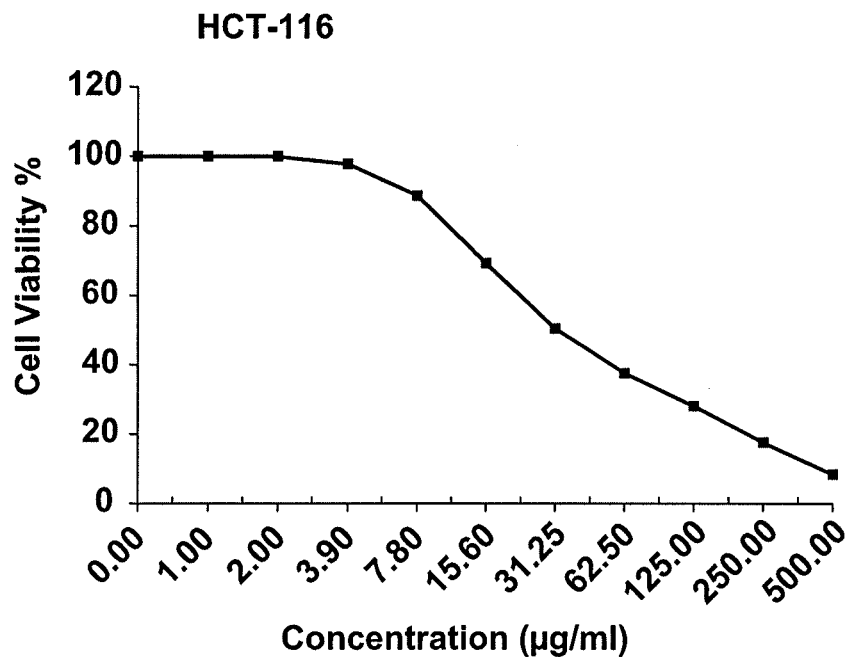
FIG. 3A is a graph of cell viability of HCT-116 (Colon carcinoma) cells exposed to different concentrations of anticancer extracts of *Alpinia officinarum* Hance.
Figure 3B:
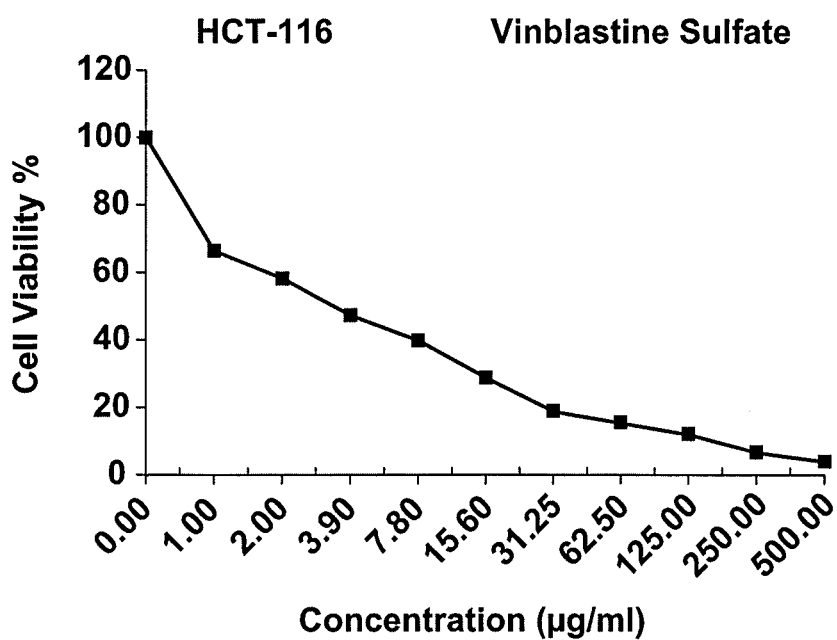
FIG. 3B is a graph of cell viability of HCT-116 cells exposed to different concentrations of the drug Vinblastine Sulfate.

The anticancer extracts of *Alpinia officinarum* Hance are ethanol extracts of *Alpinia officinarum* Hance rhizomes. The rhizomes may be washed, dried, and ground into a powder. The powder is extracted by percolation in ethanol for two days. The marc is extracted in ethanol four times, and the total alcohol extracts are concentrated into a gummy residue. The residue may then be suspended in water and filtered to produce an aqueous filtrate. The aqueous filtrate may be lyophilized to produce a dry sterile extract. This dry sterile extract may then be rehydrated in an appropriate volume of a liquid, such as water, to obtain a desired extract dose.

The *Alpinia officinarum* Hance rhizomes may be dried rhizomes harvested in Indonesia. The percolation may be performed in 95% ethanol for a period of about two days, then filtered, and the marc was extracted four times in the same manner.

As an extraction method, percolation is used to achieve complete extraction of desired constituents. Percolation allows a gravity driven flow of fresh, unsaturated solvent to flow through the source material. Percolation may be performed using any combination of equipment allowing for gravity driven extraction through a filter to progress over time. Percolation is typically performed using a percolating cone or "percolator", including an upper chamber for the filter, extraction substrate, and solvent, and a lower chamber to collect the extract solution. Alternatively, percolation may be performed using a Soxhlet extractor.

The anticancer extracts of *Alpinia officinarum* Hance may be administered to a patient in need thereof to kill cancer cells. The cancer cells may be human cancer cells. The cancer cells being targeted may be lung cancer, colon cancer, cervical cancer, or prostate cancer.

Example 1

Extraction of Alpina officinarum Hance Rhizomes

Dried rhizomes of *Alpinia officinarum* Hance harvested in Indonesia were obtained. The Rhizomes were washed, dried in an oven at about 45° C., and ground to a powder. About 200 g of the powder was then extracted by percolation in 2 liters of 95% ethanol for about 2 days. The resulting solution was then filtered over filter paper, and the marc was collected and extracted a further four times by repetition of the extraction and filtration steps. The total alcohol extracts from each extraction were then collected and concentrated in a rotary evaporator at a temperature not exceeding 25° C., producing about 35 g of gummy residue. The residue was then dissolved in about 200 ml deionized water and filtered using MicroFunnel™ Filter Funnels and a suction pump to prevent microbial contamination, producing an aqueous filtrate. The aqueous filtrate was then lyophilized, producing about 20 g of dry sterile extract. This extract was then diluted ten times and tested for anticancer activity and toxicity.

Example 2

Anticancer Testing

Briefly, the cell lines were suspended in medium at concentration of about $5 \times 10^4$ cells per well in Corning® 96-well tissue culture plates and incubated for about 24 hours. Extracts prepared according to Example 1 were rehydrated, diluted ten times, and each dilution was added to a well of a 96-well plate (using six replicates). Six vehicle controls with media or 0.5% DMSO were run for each 96 well plate as a control. After incubation for about 24 hours, the number of viable cells was determined by the MTT assay method. Briefly, the media was removed from the 96-well plates and replaced with about 100 µl of fresh culture RPMI 1640 medium without phenol red, then about 10 µl of about 12 mM MTT (Sigma) stock solution (5 mg of MTT in about 1 mL of PBS) was added to each well, including the untreated controls. The 96-well plates were then incubated at about 37° C. and at about 5% $CO_2$ for about 4 hours. An 85 µl aliquot of the media was removed from the wells, and 50 µl of DMSO was added to each well and mixed thoroughly with the pipette and incubated at about 37° C. for about 10 minutes. The optical density was measured at 590 nm with a microplate reader to determine the number of viable cells. The percentage of viability was calculated as: (ODt/ODc)× 100%, where ODt is the mean optical density of wells treated with the tested sample and ODe is the mean optical density of untreated cells.

The relation between surviving cells and extract concentration was plotted to obtain the survival curve of each tumor cell line after treatment with the specified extract. The 50% inhibitory concentration ($IC_{50}$), the concentration required to cause toxic effects in 50% of intact cells, was estimated from graphic plots of the dose response curve for each concentration using Graphpad Prism software (San Diego, Calif. USA).

The in vitro antitumor activities of *Alpinia officinarum* Hance extract were evaluated on five cell lines. The results obtained exhibited direct cytotoxic effect with a dose-dependent effect (FIGS. 1A-5A and Table 1) with variable inhibiting effect on the growth of the listed cell lines, as compared to vinblastine sulfate (FIGS. 1B-5B and Table 1).

The highest anticancer effect of *Alpinia officinarum* Hance, was recorded on A-549 (Lung carcinoma) cells and CACO (colorectal carcinoma) cells (FIGS. 1A-2B). The $IC_{50}$ results were 6.72±0.5 and 7.6±0.3 µg/ml for A-549 and CACO, respectively. These effects were improved when compared to the drug vinblastine sulfate, which had an $IC_{50}$ of 24.6±0.7 and of 30.3±1.4 µg/ml for A-549 and CACO, respectively.

Figure 4A:
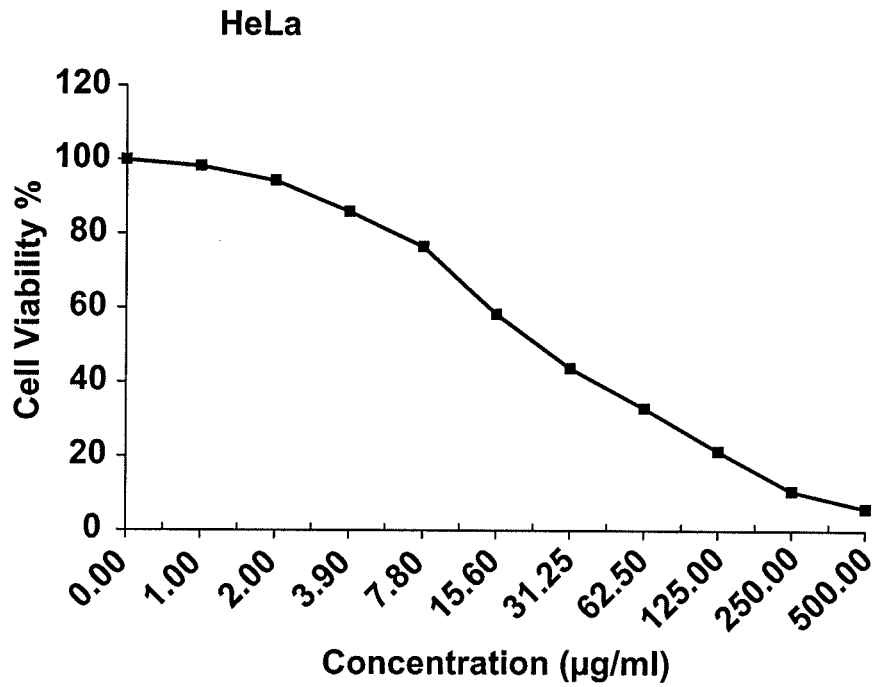
FIG. 4A is a graph of cell viability of HeLa (Cervical carcinoma) cells exposed to different concentrations of anticancer extracts of *Alpinia officinarum* Hance.
Figure 4B:
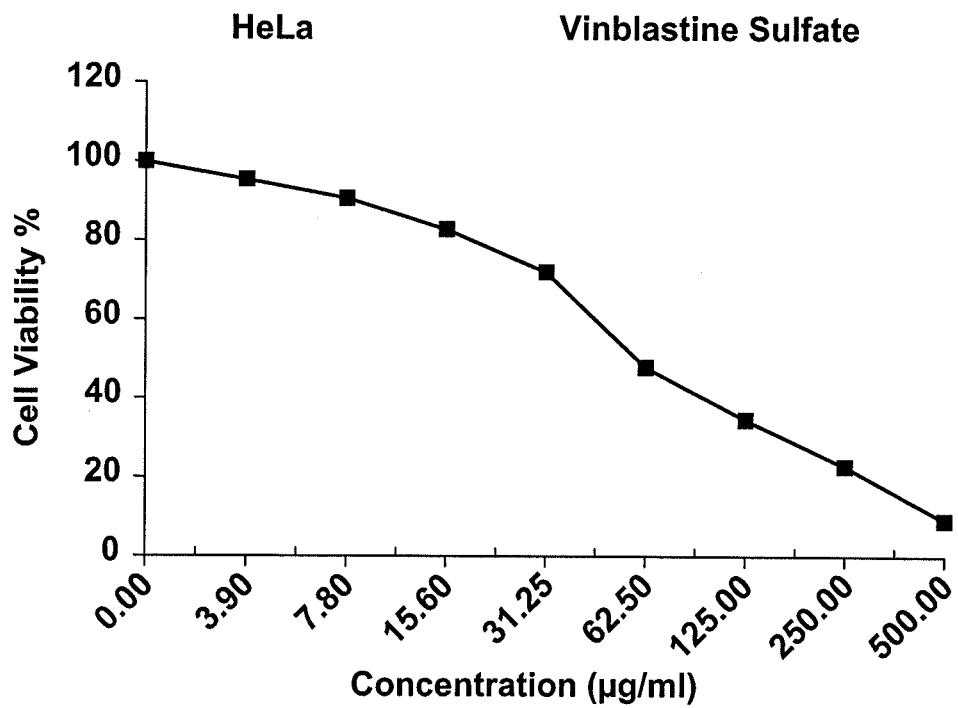
FIG. 4B is a graph of cell viability of HeLa cells exposed to different concentrations of the drug Vinblastine Sulfate.

The extracts demonstrated promising results for inhibiting the other three cell lines (HCT-116 (Colon carcinoma), HeLa (Cervical carcinoma), and PC3 (prostate cancer)). The $IC_{50}$ of the extract in HeLa (FIG. 4A) was improved (24.5±1.1 µg/ml) when compared to vinblastine sulfate (59.7±2.1 µg/ml) (FIG. 4B).

Figure 5A:
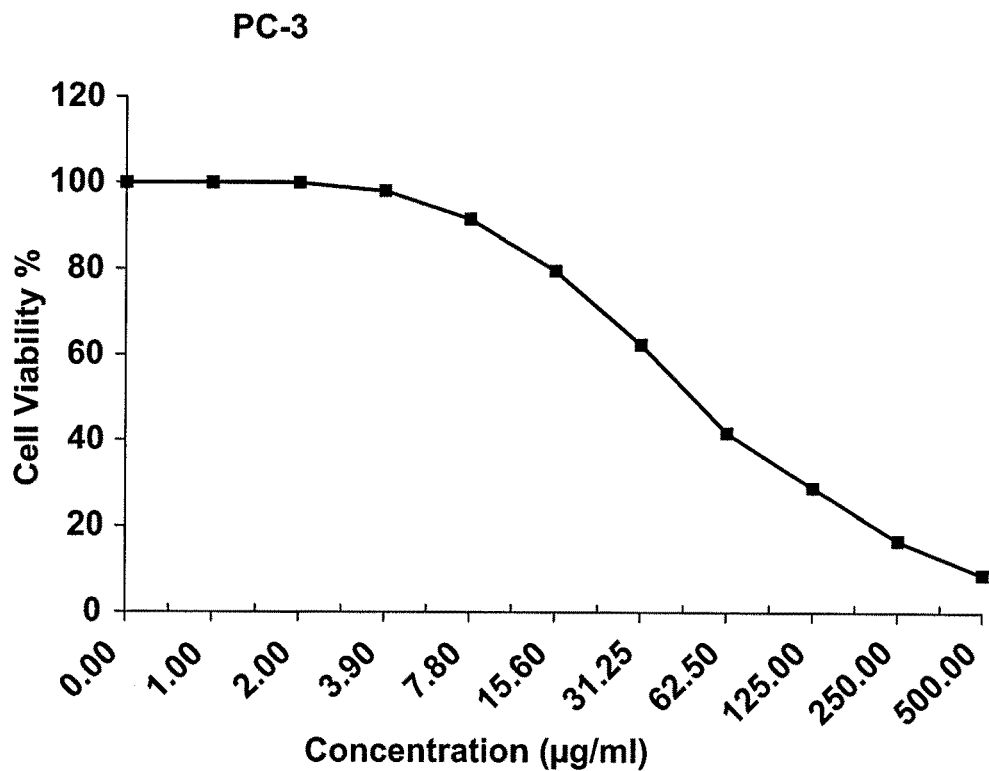
FIG. 5A is a graph of cell viability of PC3 (prostate cancer) cells exposed to different concentrations of anticancer extracts of *Alpinia officinarum* Hance.
Figure 5B:
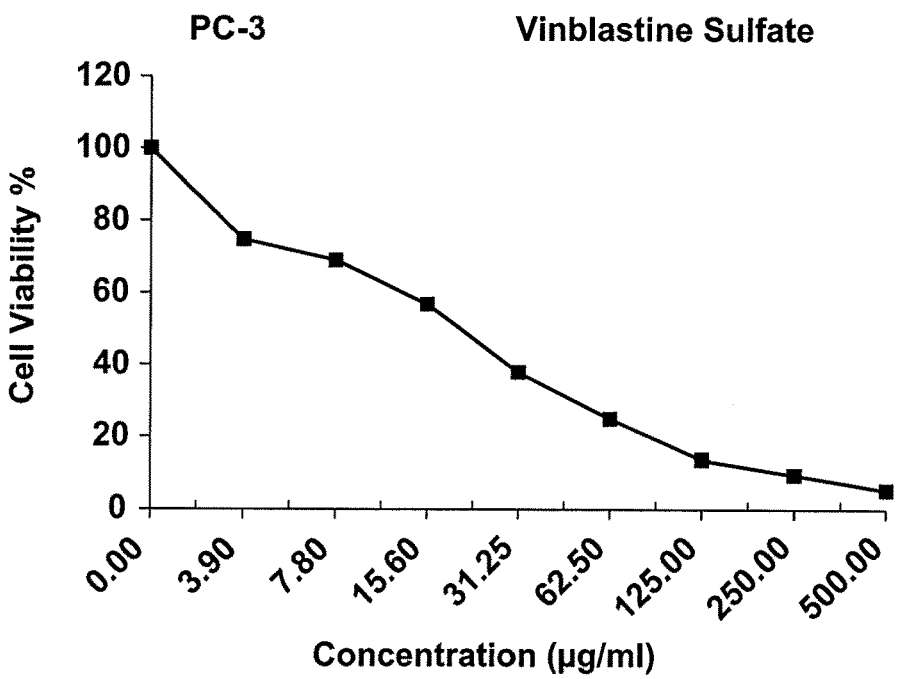
FIG. 5B is a graph of cell viability of PC3 cells exposed to different concentrations of the drug Vinblastine Sulfate.

The lowest effect was recorded on PC3 (prostate cancer), but the recorded $IC_{50}$ of 50±2.4 µg/ml (FIG. 5A) still appears promising when compared with the standard drug, vinblastine sulfate ($IC_{50}$ 21.2±0.9 µg/ml) (FIG. 5B).

TABLE 1

$IC_{50}$ values of *Alpinia officinarum* Hance rhizome extract v. vinblastine sulfate

| Cell Line | Total Alcohol Extract | Vinblastine Sulfate |
| --- | --- | --- |
| A-549 (Lung carcinoma) | 6.72 ± 0.5 | 24.6 ± 0.7 |
| CACO (Colorectal carcinoma) | 7.6 ± 0.3 | 30.3 ± 1.4 |
| HCT-116 (Colon carcinoma) | 32.3 ± 1.1 | 3.5 ± 0.2 |
| Hela (Cervical carcinoma) | 24.5 ± 1.1 | 59.7 ± 2.1 |
| Pc3 (Prostate cancer) | 50 ± 2.4 | 21.2 ± 0.9 |

Example 3

Toxicity Testing

Dried alcohol extracts of *Alpinia officinarum* Hance rhizomes prepared according to Example 1 were suspended in distilled water (freshly just before administration) using drops of Tween 80 as emulsifying agent. The suspended extracts were then given to animals orally at doses ranging from about 500 mg/kg to about 5,000 mg/kg to measure the median lethal dose ($LD_{50}$). Therefore, $LD_{50}$ of the tested extracts, up to 5000 mg/kg, is considered safe for human use For determination of sub-chronic toxicity, rats were divided into 2 groups each of 6 rats. The first group was orally administrated the vehicle to act as a control, while the second group was orally administered suspended extracts at doses of about 500 mg/kg per day for 15 days. After the examination period, sera were collected to test for liver and kidney function.

All values are expressed as mean±S.D. Comparisons between means were carried out using a one-way ANOVA test, followed by the Tukey HSD test using SPSS, version 14 (SPSS, Chicago, Ill.). Differences at p<0.05 were considered statistically significant The sub-chronic toxicity testing also supported the safety of the rhizome extract. The oral dose of about 500 mg/kg per day did not affect the levels of ALT, AST, total bilirubin, total proteins, albumin, urea, and creatinine as compared to the control (Table 2). Therefore, the extracts are not considered hepatotoxic.

TABLE 2

Sub-chronic Toxicity Testing Results

|  | ALT (U/L) | AST (U/L) | Total Bilirubin (mg/dL) | Total Protein (g/dL) | Albumin (g/dL) | Urea (mg./dL) | Creatine (mg/dL) |
|---|---|---|---|---|---|---|---|
| Control | 59.15 ± 1.3 | 48.60 ± 1.2 | 1.70 ± 0.6 | 8.70 ± 0.8 | 3.9 ± 0.3 | 37.66 ± 1.4 | 0.49 ± 0.6 |
| Extract | 58.12 ± 1.1 | 47.91 ± 1.3 | 1.69 ± 0.2 | 8.50 ± 0.5 | 3.8 ± 0.4 | 36.53 ± 1.5 | 0.50 ± 0.5 |

It is to be understood that the anticancer extracts of *Alpina officinarum* Hance are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of producing an anticancer extract of *Alpinia officinarum* Hance, comprising the sequential steps of:
    obtaining *Alpinia officinarum* Hance rhizomes;
    washing the rhizomes and drying the rhizomes in an oven at about 45° C.;
    grinding only the rhizomes into a powder;
    extracting the powder by percolation in 95% ethanol for two days to produce an ethanol extract;
    concentrating the ethanol extract to form a residue, wherein the step of concentrating the ethanol extract further comprises concentrating the ethanol extract in a rotary evaporator at a temperature not exceeding 25° C.;
    suspending the residue in deionized water;
    filtering the suspension to produce an aqueous filtrate, discarding any solid matter; and
    as the final step, lyophilizing the aqueous filtrate to produce a dry sterile extract.

2. The method of producing an anticancer extract of *Alpinia officinarum* Hance according to claim 1, wherein said step of extracting the powder comprises extracting about 200 g of said rhizome powder by percolation in 2 liters of 95% ethanol.

3. The method of producing an anticancer extract of *Alpinia officinarum* Hance according to claim 1, further comprising the steps of:
    filtering the ethanol extract with filter paper to obtain filtrate and marc;
    collecting the filtrate;
    extracting the marc left by the filtering step by percolating in ethanol to obtain additional ethanol extract;
    repeating the filtering, collecting, and extracting the marc steps on the additional ethanol extract three additional times to collect four filtrates of ethanol extract; and
    combining the four filtrates of ethanol extract prior to said step of concentrating the ethanol extract.

4. The method of producing an anticancer extract of *Alpinia officinarum* Hance according to claim 1, wherein said *Alpinia officinarum* Hance rhizomes are rhizomes harvested in Indonesia.

* * * * *